US012620496B2

(12) United States Patent
Gong et al.

(10) Patent No.: US 12,620,496 B2
(45) Date of Patent: May 5, 2026

(54) SIMULATED TRAINING DATA GENERATION FOR A MULTI-ARMED BANDIT MODEL

(71) Applicant: Maplebear Inc., San Francisco, CA (US)

(72) Inventors: Xiao Gong, San Francisco, CA (US); Konrad Gustav Miziolek, San Francisco, CA (US)

(73) Assignee: Maplebear Inc., San Francisco, CA (US)

( * ) Notice: Subject to any disclaimer, the term of this patent is extended or adjusted under 35 U.S.C. 154(b) by 480 days.

(21) Appl. No.: 18/175,723

(22) Filed: Feb. 28, 2023

(65) Prior Publication Data

US 2024/0290501 A1 Aug. 29, 2024

(51) Int. Cl.
*G16H 50/50* (2018.01)
*G06N 3/08* (2023.01)

(52) U.S. Cl.
CPC .............. *G16H 50/50* (2018.01); *G06N 3/08* (2013.01)

(58) Field of Classification Search
CPC ................................ G16H 50/50; G06N 3/08
See application file for complete search history.

(56) References Cited

U.S. PATENT DOCUMENTS

| | | | | |
|---|---|---|---|---|
| 8,688,610 B1 * | 4/2014 | Weisberg | .............. | G16H 20/10 |
| | | | | 706/46 |
| 2017/0083679 A1 * | 3/2017 | Feder | ..................... | G16H 50/30 |

| | | | | |
|---|---|---|---|---|
| 2020/0074573 A1 * | 3/2020 | Op Den Buijs | ....... | G06Q 10/10 |
| 2020/0125586 A1 | 4/2020 | Rezaeian et al. | | |
| 2022/0335505 A1 | 10/2022 | Prasad et al. | | |
| 2023/0068634 A1 | 3/2023 | Ruan et al. | | |
| 2023/0351465 A1 * | 11/2023 | Miziolek | ............ | G06Q 30/0206 |
| 2023/0368236 A1 * | 11/2023 | Drerup | ............... | G06Q 30/0211 |
| 2024/0104493 A1 | 3/2024 | Faturechi et al. | | |
| 2024/0202784 A1 | 6/2024 | Hayes et al. | | |
| 2024/0289731 A1 | 8/2024 | Xu et al. | | |

OTHER PUBLICATIONS

D. Daria Dzyabura, John R. Hauser (2019) Recommending Products When Consumers Learn Their Preference Weights. Marketing Science 38(3):417-441. (Year: 2019).*
United States Office Action, U.S. Appl. No. 18/175,720, filed Apr. 16, 2025, 9 pages.

* cited by examiner

*Primary Examiner* — Amber A Misiaszek
(74) *Attorney, Agent, or Firm* — Fenwick & West LLP

(57) ABSTRACT

An online system adjusts a guardrail setting used by a user treatment engine based on conditions faced by the online system. The online system simulates the performance of the user treatment engine using different candidate guardrail settings and computes a score for each of the guardrail settings based on the performance of the user treatment engine using each of the guardrail settings. The online system selects a new guardrail setting for the user treatment engine based on the performance scores for the candidate guardrail settings. Furthermore, the online system generates simulated training examples to initially train a user treatment engine. The online system uses a treatment performance model to simulate the effect of treatments applied to users and generates simulated training examples based on the predicted effect of the treatments. The online system retrains the user treatment engine on real training examples that are generated based on actual treatments.

20 Claims, 9 Drawing Sheets

Predicted Orders in Next Hour: 100 } 530

Predicted Orders with Guardrail at:

| 510 | 520 | 500 |
| --- | --- | --- |
| Cap at 5% | 83.2 | 6.8 |
| Cap at 10% | 91.6 | 8.3 |
| Cap at 15% | 105.8 | 9.1 |
| Cap at 20% | 130.7 | 5.4 |

FIG. 5

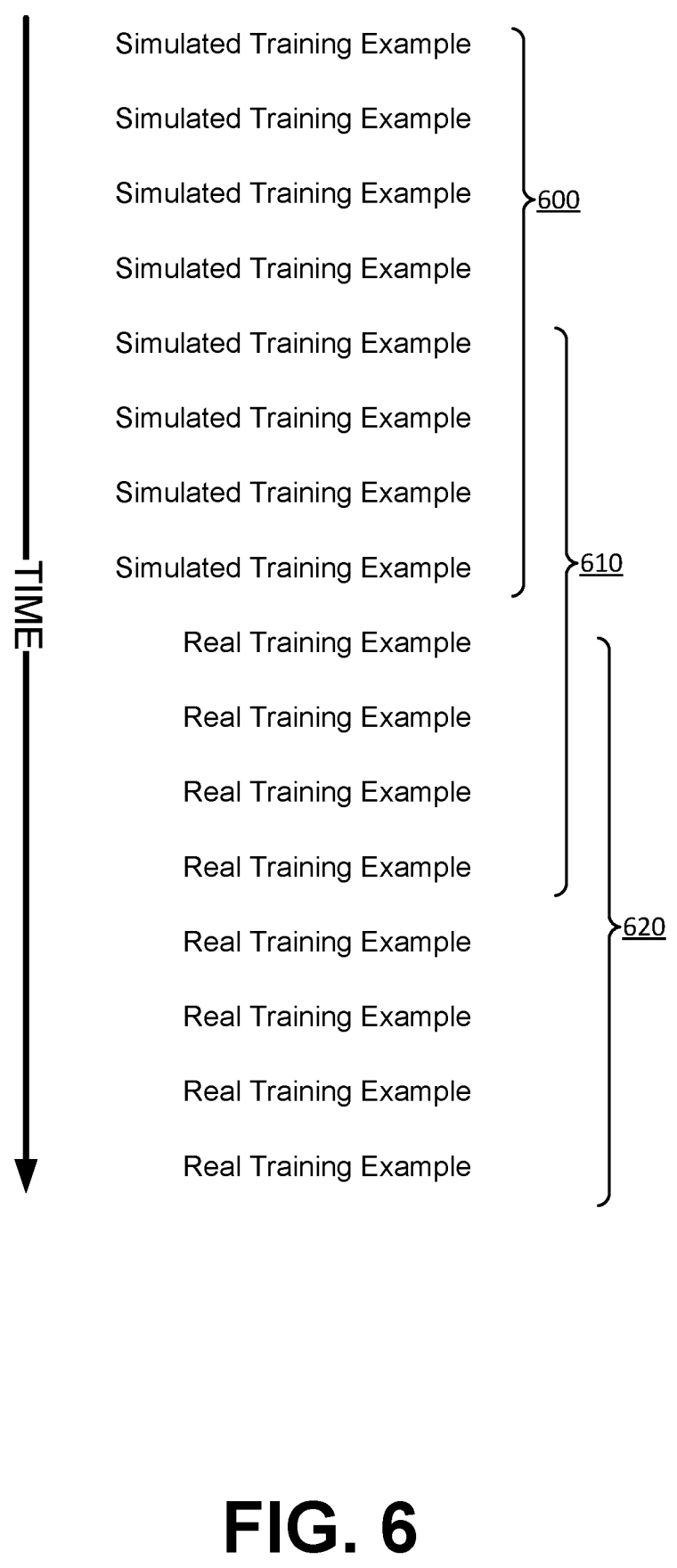

TIME

Simulated Training Example
Simulated Training Example
Simulated Training Example ⟩ 600
Simulated Training Example Simulated Training Example
Simulated Training Example
Simulated Training Example
Simulated Training Example ⟩ 610

Real Training Example
Real Training Example
Real Training Example
Real Training Example Real Training Example
Real Training Example ⟩ 620
Real Training Example
Real Training Example

FIG. 6

SIMULATED TRAINING DATA GENERATION FOR A MULTI-ARMED BANDIT MODEL

BACKGROUND

Online systems, such as an online concierge system, often apply treatments to users to encourage those users to interact with the online system. For example, an online system may notify a user of new content that is available to the user or may provide incentives to a user if the user performs an interaction with the online system. When an online system has a set of candidate treatments that could be applied to a user, the online system has to balance exploring the uncertain efficacy of some of the treatments with maximizing the known efficacy of others.

An online system may use a user treatment engine to automatically balance exploration with maximization. However, treatments may incur costs to the online system for their application to users, and thus an online system must limit the treatments that the user treatment system can select. For example, the online system may use a guardrail setting that establishes a limit on which treatments (or variants thereof) a user treatment engine can select. Guardrail settings are commonly heuristics that are hardcoded by engineers to limit the actions of systems like user treatment engines, and while these heuristics may work most of the time, the proper guardrail setting for a user treatment engine can change with time. For example, in the context of an online concierge system where a user treatment engine applies treatments to pickers to encourage pickers to service orders, a guardrail setting that is too strict may cause too few pickers to be available to be assigned orders to service by the online concierge system. Similarly, a guardrail setting that is too lax may cause too many pickers to be available and incur significant costs for the online system. Furthermore, the conditions that cause a guardrail setting to be too strict or too lax can change over time, meaning that a hardcoded guardrail setting is likely to encounter these problems eventually.

Furthermore, a user treatment engine may encounter a cold start problem with the machine-learning model that the engine uses to select treatments. A user treatment engine may use a multi-armed bandit model to balance exploration and maximization for applying treatments to users. However, multi-armed bandit models commonly need to be trained on existing training examples to effectively select treatments for application to users. For example, a multi-armed bandit with no training examples may over explore the efficacy of treatments and under utilize treatments with known efficacy. Thus, an online system using a multi-armed bandit model commonly must execute the multi-armed bandit model for a certain period of time (e.g., two weeks) without using the output of the model while the system collects the necessary training data for the model to provide a useful output. Therefore, multi-armed bandit models can be slow to release to production, making iterations on those models difficult.

SUMMARY

In accordance with one or more aspects of the disclosure, an online concierge system dynamically adjusts guardrail settings for a user treatment engine that selects treatments to apply to users. A guardrail setting is a setting for the user treatment engine that limits the treatments or variants that the user treatment engine can select. For example, a guardrail setting may enforce a limit on a cost of an individual treatment, a total cost of a set of treatments, or a frequency of how often a particular treatment is selected. The user treatment engine selects treatments to apply to users based on the guardrail setting, and the online concierge system applies the selected treatments to users.

The online concierge system occasionally adjusts the guardrail settings for the user treatment engine by selecting a new guardrail setting for the user treatment engine from a set of candidate guardrail settings. The online concierge system computes a performance score for each of the candidate guardrail settings by simulating the performance of the user treatment engine if the user treatment engine used the candidate guardrail setting. For example, the online concierge system may predict a number of orders that users would service if the user treatment engine selected treatments using a candidate guardrail setting. The online concierge system may then compare that predicted number of orders to a predicted number of future orders that the online concierge system expects to receive within some time period in the future (e.g., the next 24 hours). The online concierge system scores the performance of each candidate guardrail setting based on a difference between those numbers, i.e., based on a difference between the number of orders the online concierge system expects to receive and the predicted number of orders that would be serviced using the candidate guardrail setting. The online concierge system selects a new guardrail setting for the user treatment engine based on the respective scores of the candidate guardrail settings.

By simulating the performance of guardrail settings, the online concierge system can dynamically update the guardrail settings used for the user treatment engine and thus can adapt the guardrail settings to changing conditions that the online concierge system faces.

In accordance with one or more aspects of the disclosure, an online concierge system uses a treatment performance model to generate simulated training examples for a user treatment engine. A treatment performance model is a machine-learning model (e.g., a neural network) that is trained to predict a number of orders to be serviced by a user within a time period after (e.g., next 24 hours) a treatment is applied to the user. The online concierge system uses the treatment performance model to generate a set of simulated training examples for an initialized user treatment engine. A simulated training example is a training example for the user treatment engine that represents a simulated treatment applied to a user. The simulated training example includes user data for a user, treatment data for a treatment to simulate application to the user, and a predicted number of orders to be serviced by the user if the treatment had been applied to the user. The online concierge system uses these simulated training examples to train the user treatment engine and uses the user treatment engine to select treatments to apply to users.

As the user treatment engine selects treatments to apply to users, the online concierge system generates real training examples based on the results of the treatments applied to users. These real training examples include treatment data for a treatment applied to a user, user data for the user to whom the treatment was applied, and a number of orders serviced by the user within a time period after the treatment was applied to the user. The online concierge system retrains the user treatment engine based on the generated real training examples. The online concierge system may retrain the user treatment engine based on a combined set of training examples that includes the real training examples and a subset of the simulated training examples. As the online concierge system generates more real training examples based on treatments selected by the user treatment engine, the online concierge system may use more real training examples to retrain the user treatment engine and fewer simulated training examples. Eventually, the online concierge system may use entirely real training examples and no simulated training examples after a certain time period.

By generating simulated training examples to initially train a user treatment engine, the online concierge system can avoid the cold-start problem that may be experienced when using a multi-armed bandit model for selecting treatments to apply to users. Thus, a user treatment engine can be deployed more quickly once initialized, thereby allowing engineers to iterate on models for the user treatment engine more effectively.

BRIEF DESCRIPTION OF THE DRAWINGS

FIG. 5 illustrates example performance scores for a set of candidate guardrail settings, in accordance with one or more embodiments.

FIG. 6 illustrates example sets of training examples that may be used to train or retrain a user treatment engine, in accordance with one or more embodiments.

DETAILED DESCRIPTION

Figure 1:
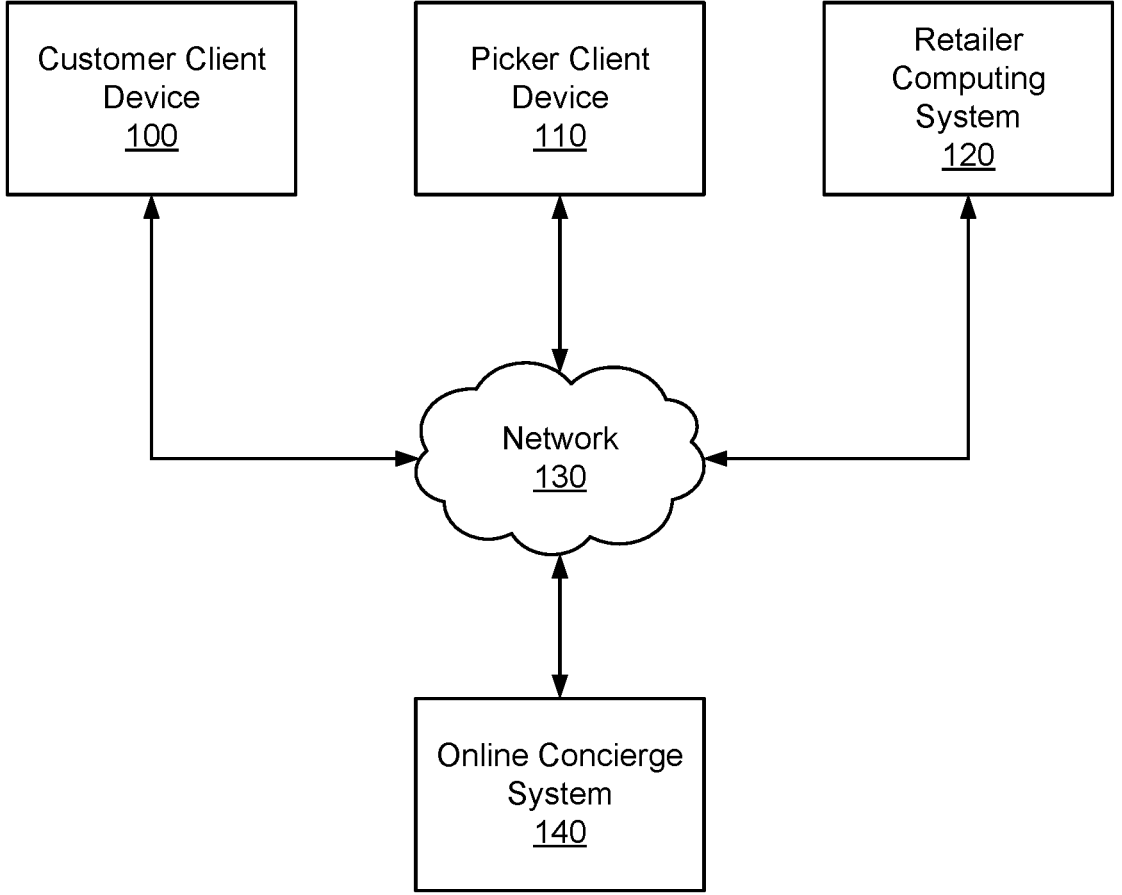
FIG. 1 illustrates an example system environment for an online concierge system, in accordance with one or more embodiments.

FIG. 1 illustrates an example system environment for an online concierge system 140, in accordance with one or more embodiments. The system environment illustrated in FIG. 1 includes a customer client device 100, a picker client device 110, a retailer computing system 120, a network 130, and an online concierge system 140. Alternative embodiments may include more, fewer, or different components from those illustrated in FIG. 1, and the functionality of each component may be divided between the components differently from the description below. Additionally, each component may perform their respective functionalities in response to a request from a human, or automatically without human intervention.

As used herein, customers, pickers, and retailers may be generically referred to as "users" of the online concierge system 140. Additionally, while one customer client device 100, picker client device 110, and retailer computing system 120 are illustrated in FIG. 1, any number of customers, pickers, and retailers may interact with the online concierge system 140. As such, there may be more than one customer client device 100, picker client device 110, or retailer computing system 120.

The customer client device 100 is a client device through which a customer may interact with the picker client device 110, the retailer computing system 120, or the online concierge system 140. The customer client device 100 can be a personal or mobile computing device, such as a smartphone, a tablet, a laptop computer, or desktop computer. In some embodiments, the customer client device 100 executes a client application that uses an application programming interface (API) to communicate with the online concierge system 140.

A customer uses the customer client device 100 to place an order with the online concierge system 140. An order specifies a set of items to be delivered to the customer. An "item", as used herein, means a good or product that can be provided to the customer through the online concierge system 140. The order may include item identifiers (e.g., a stock keeping unit or a price look-up code) for items to be delivered to the user and may include quantities of the items to be delivered. Additionally, an order may further include a delivery location to which the ordered items are to be delivered and a timeframe during which the items should be delivered. In some embodiments, the order also specifies one or more retailers from which the ordered items should be collected.

The customer client device 100 presents an ordering interface to the customer. The ordering interface is a user interface that the customer can use to place an order with the online concierge system 140. The ordering interface may be part of a client application operating on the customer client device 100. The ordering interface allows the customer to search for items that are available through the online concierge system 140 and the customer can select which items to add to a "shopping list." A "shopping list," as used herein, is a tentative set of items that the user has selected for an order but that has not yet been finalized for an order. The ordering interface allows a customer to update the shopping list, e.g., by changing the quantity of items, adding or removing items, or adding instructions for items that specify how the item should be collected.

The customer client device 100 may receive additional content from the online concierge system 140 to present to a customer. For example, the customer client device 100 may receive coupons, recipes, or item suggestions. The customer client device 100 may present the received additional content to the customer as the customer uses the customer client device 100 to place an order (e.g., as part of the ordering interface).

Additionally, the customer client device 100 includes a communication interface that allows the customer to communicate with a picker that is servicing the customer's order. This communication interface allows the user to input a text-based message to transmit to the picker client device 110 via the network 130. The picker client device 110 receives the message from the customer client device 100 and presents the message to the picker. The picker client device 110 also includes a communication interface that allows the picker to communicate with the customer. The picker client device 110 transmits a message provided by the picker to the customer client device 100 via the network 130. In some embodiments, messages sent between the customer client device 100 and the picker client device 110 are transmitted through the online concierge system 140. In addition to text messages, the communication interfaces of the customer client device 100 and the picker client device 110 may allow the customer and the picker to communicate through audio or video communications, such as a phone call, a voice-over-IP call, or a video call.

The picker client device 110 is a client device through which a picker may interact with the customer client device 100, the retailer computing system 120, or the online concierge system 140. The picker client device 110 can be a personal or mobile computing device, such as a smartphone, a tablet, a laptop computer, or desktop computer. In some embodiments, the picker client device 110 executes a client application that uses an application programming interface (API) to communicate with the online concierge system 140.

The picker client device 110 receives orders from the online concierge system 140 for the picker to service. A picker services an order by collecting the items listed in the order from a retailer. The picker client device 110 presents the items that are included in the customer's order to the picker in a collection interface. The collection interface is a user interface that provides information to the picker on which items to collect for a customer's order and the quantities of the items. In some embodiments, the collection interface provides multiple orders from multiple customers for the picker to service at the same time from the same retailer location. The collection interface further presents instructions that the customer may have included related to the collection of items in the order. Additionally, the collection interface may present a location of each item in the retailer location, and may even specify a sequence in which the picker should collect the items for improved efficiency in collecting items. In some embodiments, the picker client device 110 transmits to the online concierge system 140 or the customer client device 100 which items the picker has collected in real time as the picker collects the items.

The picker can use the picker client device 110 to keep track of the items that the picker has collected to ensure that the picker collects all of the items for an order. The picker client device 110 may include a barcode scanner that can determine an item identifier encoded in a barcode coupled to an item. The picker client device 110 compares this item identifier to items in the order that the picker is servicing, and if the item identifier corresponds to an item in the order, the picker client device 110 identifies the item as collected. In some embodiments, rather than or in addition to using a barcode scanner, the picker client device 110 captures one or more images of the item and determines the item identifier for the item based on the images. The picker client device 110 may determine the item identifier directly or by transmitting the images to the online concierge system 140. Furthermore, the picker client device 110 determines a weight for items that are priced by weight. The picker client device 110 may prompt the picker to manually input the weight of an item or may communicate with a weighing system in the retailer location to receive the weight of an item.

When the picker has collected all of the items for an order, the picker client device 110 instructs a picker on where to deliver the items for a customer's order. For example, the picker client device 110 displays a delivery location from the order to the picker. The picker client device 110 also provides navigation instructions for the picker to travel from the retailer location to the delivery location. Where a picker is servicing more than one order, the picker client device 110 identifies which items should be delivered to which delivery location. The picker client device 110 may provide navigation instructions from the retailer location to each of the delivery locations. The picker client device 110 may receive one or more delivery locations from the online concierge system 140 and may provide the delivery locations to the picker so that the picker can deliver the corresponding one or more orders to those locations. The picker client device 110 may also provide navigation instructions for the picker from the retailer location from which the picker collected the items to the one or more delivery locations.

In some embodiments, the picker client device 110 tracks the location of the picker as the picker delivers orders to delivery locations. The picker client device 110 collects location data and transmits the location data to the online concierge system 140. The online concierge system 140 may transmit the location data to the customer client device 100 for display to the customer such that the customer can keep track of when their order will be delivered. Additionally, the online concierge system 140 may generate updated navigation instructions for the picker based on the picker's location. For example, if the picker takes a wrong turn while traveling to a delivery location, the online concierge system 140 determines the picker's updated location based on location data from the picker client device 110 and generates updated navigation instructions for the picker based on the updated location.

In one or more embodiments, the picker is a single person who collects items for an order from a retailer location and delivers the order to the delivery location for the order. Alternatively, more than one person may serve the role as a picker for an order. For example, multiple people may collect the items at the retailer location for a single order. Similarly, the person who delivers an order to its delivery location may be different from the person or people who collected the items from the retailer location. In these embodiments, each person may have a picker client device 110 that they can use to interact with the online concierge system 140.

Additionally, while the description herein may primarily refer to pickers as humans, in some embodiments, some or all of the steps taken by the picker may be automated. For example, a semi- or fully-autonomous robot may collect items in a retailer location for an order and an autonomous vehicle may deliver an order to a customer from a retailer location.

The retailer computing system 120 is a computing system operated by a retailer that interacts with the online concierge system 140. As used herein, a "retailer" is an entity that operates a "retailer location," which is a store, warehouse, or other building from which a picker can collect items. The retailer computing system 120 stores and provides item data to the online concierge system 140 and may regularly update the online concierge system 140 with updated item data. For example, the retailer computing system 120 provides item data indicating which items are available at a retailer location and the quantities of those items. Additionally, the retailer computing system 120 may transmit updated item data to the online concierge system 140 when an item is no longer available at the retailer location. Additionally, the retailer computing system 120 may provide the online concierge system 140 with updated item prices, sales, or availabilities. Additionally, the retailer computing system 120 may receive payment information from the online concierge system 140 for orders serviced by the online concierge system 140. Alternatively, the retailer computing system 120 may provide payment to the online concierge system 140 for some portion of the overall cost of a user's order (e.g., as a commission).

The customer client device 100, the picker client device 110, the retailer computing system 120, and the online concierge system 140 can communicate with each other via the network 130. The network 130 is a collection of computing devices that communicate via wired or wireless connections. The network 130 may include one or more local area networks (LANs) or one or more wide area networks (WANs). The network 130, as referred to herein, is an inclusive term that may refer to any or all of standard layers used to describe a physical or virtual network, such as the physical layer, the data link layer, the network layer, the transport layer, the session layer, the presentation layer, and the application layer. The network 130 may include physical media for communicating data from one computing device to another computing device, such as MPLS lines, fiber optic cables, cellular connections (e.g., 3G, 4G, or 5G spectra), or satellites. The network 130 also may use networking protocols, such as TCP/IP, HTTP, SSH, SMS, or FTP, to transmit data between computing devices. In some embodiments, the network 130 may include Bluetooth or near-field communication (NFC) technologies or protocols for local communications between computing devices. The network 130 may transmit encrypted or unencrypted data.

The online concierge system 140 is an online system by which customers can order items to be provided to them by a picker from a retailer. The online concierge system 140 receives orders from a customer client device 100 through the network 130. The online concierge system 140 selects a picker to service the customer's order and transmits the order to a picker client device 110 associated with the picker. The picker collects the ordered items from a retailer location and delivers the ordered items to the customer. The online concierge system 140 may charge a customer for the order and provides portions of the payment from the customer to the picker and the retailer.

As an example, the online concierge system 140 may allow a customer to order groceries from a grocery store retailer. The customer's order may specify which groceries they want delivered from the grocery store and the quantities of each of the groceries. The customer's client device 100 transmits the customer's order to the online concierge system 140 and the online concierge system 140 selects a picker to travel to the grocery store retailer location to collect the groceries ordered by the customer. Once the picker has collected the groceries ordered by the customer, the picker delivers the groceries to a location transmitted to the picker client device 110 by the online concierge system 140. The online concierge system 140 is described in further detail below with regards to FIG. 2.

Figure 2:
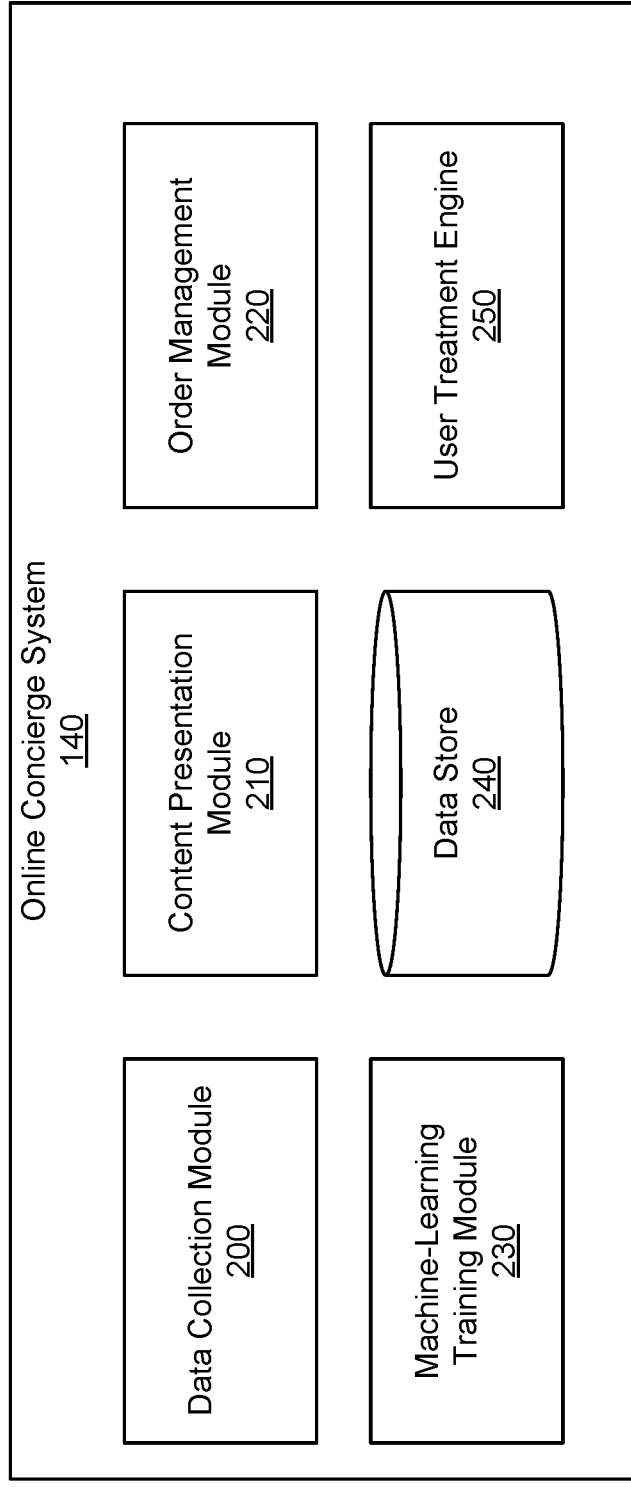
FIG. 2 illustrates an example system architecture for an online concierge system, in accordance with one or more embodiments.

FIG. 2 illustrates an example system architecture for an online concierge system 140, in accordance with some embodiments. The system architecture illustrated in FIG. 2 includes a data collection module 200, a content presentation module 210, an order management module 220, a machine learning training module 230, a data store 240, and a user treatment engine 250. Alternative embodiments may include more, fewer, or different components from those illustrated in FIG. 2, and the functionality of each component may be divided between the components differently from the description below. Additionally, each component may perform their respective functionalities in response to a request from a human, or automatically without human intervention.

The data collection module 200 collects data used by the online concierge system 140 and stores the data in the data store 240. The data collection module 200 may only collect data describing a user if the user has previously explicitly consented to the online concierge system 140 collecting data describing the user. Additionally, the data collection module 200 may encrypt all data, including sensitive or personal data, describing users.

For example, the data collection module 200 collects customer data, which is information or data that describe characteristics of a customer. Customer data may include a customer's name, address, shopping preferences, favorite items, or stored payment instruments. The customer data also may include default settings established by the customer, such as a default retailer/retailer location, payment instrument, delivery location, or delivery timeframe. The data collection module 200 may collect the customer data from sensors on the customer client device 100 or based on the customer's interactions with the online concierge system 140.

The data collection module 200 also collects item data, which is information or data that identifies and describes items that are available at a retailer location. The item data may include item identifiers for items that are available and may include quantities of items associated with each item identifier. Additionally, item data may also include attributes of items such as the size, color, weight, stock keeping unit (SKU), or serial number for the item. The item data may further include purchasing rules associated with each item, if they exist. For example, age-restricted items such as alcohol and tobacco are flagged accordingly in the item data. Item data may also include information that is useful for predicting the availability of items in retailer locations. For example, for each item-retailer combination (a particular item at a particular warehouse), the item data may include a time that the item was last found, a time that the item was last not found (a picker looked for the item but could not find it), the rate at which the item is found, or the popularity of the item. The data collection module 200 may collect item data from a retailer computing system 120, a picker client device 110, or the customer client device 100.

An item category is a set of items that are a similar type of item. Items in an item category may be considered to be equivalent to each other or that may be replacements for each other in an order. For example, different brands of sourdough bread may be different items, but these items may be in a "sourdough bread" item category. The item categories may be human-generated and human-populated with items. The item categories also may be generated automatically by the online concierge system 140 (e.g., using a clustering algorithm).

The data collection module 200 also collects picker data, which is information or data that describes characteristics of pickers. For example, the picker data for a picker may include the picker's name, the picker's location, how often the picker has services orders for the online concierge system 140, a customer rating for the picker, which retailers the picker has collected items at, or the picker's previous shopping history. Additionally, the picker data may include preferences expressed by the picker, such as their preferred retailers to collect items at, how far they are able to travel to deliver items to a customer, how many items they are able to collect at a time, timeframes within which the picker is able to service orders, or payment information by which the picker is to be paid for servicing orders (e.g., a bank account). The data collection module 200 collects picker data from sensors of the picker client device 110 or from the picker's interactions with the online concierge system 140.

Additionally, the data collection module 200 collects order data, which is information or data that describes characteristics of an order. For example, order data may include item data for items that are included in the order, a delivery location for the order, a customer associated with the order, a retailer location from which the customer wants the ordered items collected, or a timeframe within which the customer wants the order delivered. Order data may further include information describing how the order was serviced, such as which picker serviced the order, when the order was delivered, or a rating that the customer gave the delivery of the order. In some embodiments, the order data includes user data for users associated with the order, such as customer data for a customer who placed the order or picker data for a picker who serviced the order.

The content presentation module 210 selects content for presentation to a customer. For example, the content presentation module 210 selects which items to present to a customer while the customer is placing an order. The content presentation module 210 generates and transmits the ordering interface for the customer to order items. The content presentation module 210 populates the ordering interface with items that the customer may select for adding to their order. In some embodiments, the content presentation module 210 presents a catalog of all items that are available to the customer, which the customer can browse to select items to order. The content presentation module 210 also may identify items that the customer is most likely to order and present those items to the customer. For example, the content presentation module 210 may score items and rank the items based on their scores. The content presentation module 210 displays the items with scores that exceed some threshold (e.g., the top n items or the p percentile of items).

The content presentation module 210 may use an item selection model to score items for presentation to a customer. An item selection model is a machine learning model that is trained to score items for a customer based on item data for the items and customer data for the customer. For example, the item selection model may be trained to determine a likelihood that the customer will order the item. In some embodiments, the item selection model uses item embeddings describing items and customer embeddings describing customers to score items. These item embeddings and customer embeddings may be generated by separate machine learning models and may be stored in the data store 240.

In some embodiments, the content presentation module 210 scores items based on a search query received from the customer client device 100. A search query is free text for a word or set of words that indicate items of interest to the customer. The content presentation module 210 scores items based on a relatedness of the items to the search query. For example, the content presentation module 210 may apply natural language processing (NLP) techniques to the text in the search query to generate a search query representation (e.g., an embedding) that represents characteristics of the search query. The content presentation module 210 may use the search query representation to score candidate items for presentation to a customer (e.g., by comparing a search query embedding to an item embedding).

In some embodiments, the content presentation module 210 scores items based on a predicted availability of an item. The content presentation module 210 may use an availability model to predict the availability of an item. An availability model is a machine learning model that is trained to predict the availability of an item at a retailer location. For example, the availability model may be trained to predict a likelihood that an item is available at a retailer location or may predict an estimated number of items that are available at a retailer location. The content presentation module 210 may weight the score for an item based on the predicted availability of the item. Alternatively, the content presentation module 210 may filter out items from presentation to a customer based on whether the predicted availability of the item exceeds a threshold.

The order management module 220 that manages orders for items from customers. The order management module 220 receives orders from a customer client device 100 and assigns the orders to pickers for service based on picker data. For example, the order management module 220 assigns an order to a picker based on the picker's location and the location of the retailer from which the ordered items are to be collected. The order management module 220 may also assign an order to a picker based on how many items are in the order, a vehicle operated by the picker, the delivery location, the picker's preferences on how far to travel to deliver an order, the picker's ratings by customers, or how often a picker agrees to service an order.

In some embodiments, the order management module 220 determines when to assign an order to a picker based on a delivery timeframe requested by the customer with the order. The order management module 220 computes an estimated amount of time that it would take for a picker to collect the items for an order and deliver the ordered item to the delivery location for the order. The order management module 220 assigns the order to a picker at a time such that, if the picker immediately services the order, the picker is likely to deliver the order at a time within the timeframe. Thus, when the order management module 220 receives an order, the order management module 220 may delay in assigning the order to a picker if the timeframe is far enough in the future.

When the order management module 220 assigns an order to a picker, the order management module 220 transmits the order to the picker client device 110 associated with the picker. The order management module 220 may also transmit navigation instructions from the picker's current location to the retailer location associated with the order. If the order includes items to collect from multiple retailer locations, the order management module 220 identifies the retailer locations to the picker and may also specify a sequence in which the picker should visit the retailer locations.

The order management module 220 may track the location of the picker through the picker client device 110 to determine when the picker arrives at the retailer location. When the picker arrives at the retailer location, the order management module 220 transmits the order to the picker client device 110 for display to the picker. As the picker uses the picker client device 110 to collect items at the retailer location, the order management module 220 receives item identifiers for items that the picker has collected for the order. In some embodiments, the order management module 220 receives images of items from the picker client device 110 and applies computer-vision techniques to the images to identify the items depicted by the images. The order management module 220 may track the progress of the picker as the picker collects items for an order and may transmit progress updates to the customer client device 100 that describe which items have been collected for the customer's order.

In some embodiments, the order management module 220 tracks the location of the picker within the retailer location. The order management module 220 uses sensor data from the picker client device 110 or from sensors in the retailer location to determine the location of the picker in the retailer location. The order management module 220 may transmit to the picker client device 110 instructions to display a map of the retailer location indicating where in the retailer location the picker is located. Additionally, the order management module 220 may instruct the picker client device 110 to display the locations of items for the picker to collect, and may further display navigation instructions for how the picker can travel from their current location to the location of a next item to collect for an order.

The order management module 220 determines when the picker has collected all of the items for an order. For example, the order management module 220 may receive a message from the picker client device 110 indicating that all of the items for an order have been collected. Alternatively, the order management module 220 may receive item identifiers for items collected by the picker and determine when all of the items in an order have been collected. When the order management module 220 determines that the picker has completed an order, the order management module 220 transmits the delivery location for the order to the picker client device 110. The order management module 220 may also transmit navigation instructions to the picker client device 110 that specify how to travel from the retailer location to the delivery location, or to a subsequent retailer location for further item collection. The order management module 220 tracks the location of the picker as the picker travels to the delivery location for an order, and updates the customer with the location of the picker so that the customer can track the progress of their order. In some embodiments, the order management module 220 computes an estimated time of arrival for the picker at the delivery location and provides the estimated time of arrival to the customer.

In some embodiments, the order management module 220 facilitates communication between the customer client device 100 and the picker client device 110. As noted above, a customer may use a customer client device 100 to send a message to the picker client device 110. The order management module 220 receives the message from the customer client device 100 and transmits the message to the picker client device 110 for presentation to the picker. The picker may use the picker client device 110 to send a message to the customer client device 100 in a similar manner.

The order management module 220 coordinates payment by the customer for the order. The order management module 220 uses payment information provided by the customer (e.g., a credit card number or a bank account) to receive payment for the order. In some embodiments, the order management module 220 stores the payment information for use in subsequent orders by the customer. The order management module 220 computes a total cost for the order and charges the customer that cost. The order management module 220 may provide a portion of the total cost to the picker for servicing the order, and another portion of the total cost to the retailer.

The machine learning training module 230 trains machine learning models used by the online concierge system 140. The online concierge system 140 may use machine learning models to perform functionalities described herein. Example machine learning models include regression models, support vector machines, naïve bayes, decision trees, k nearest neighbors, random forest, boosting algorithms, k-means, and hierarchical clustering. The machine learning models may also include neural networks, such as perceptrons, multilayer perceptrons, convolutional neural networks, recurrent neural networks, sequence-to-sequence models, generative adversarial networks, or transformers.

Each machine learning model includes a set of parameters. A set of parameters for a machine learning model are parameters that the machine learning model uses to process an input. For example, a set of parameters for a linear regression model may include weights that are applied to each input variable in the linear combination that comprises the linear regression model. Similarly, the set of parameters for a neural network may include weights and biases that are applied at each neuron in the neural network. The machine learning training module 230 generates the set of parameters for a machine learning model by "training" the machine learning model. Once trained, the machine learning model uses the set of parameters to transform inputs into outputs.

The machine learning training module 230 trains a machine learning model based on a set of training examples. Each training example includes input data to which the machine learning model is applied to generate an output. For example, each training example may include customer data, picker data, item data, or order data. In some cases, the training examples also include a label which represents an expected output of the machine learning model. In these cases, the machine learning model is trained by comparing its output from input data of a training example to the label for the training example.

The machine learning training module 230 may apply an iterative process to train a machine learning model whereby the machine learning training module 230 trains the machine learning model on each of the set of training examples. To train a machine learning model based on a training example, the machine learning training module 230 applies the machine learning model to the input data in the training example to generate an output. The machine learning training module 230 scores the output from the machine learning model using a loss function. A loss function is a function that generates a score for the output of the machine learning model such that the score is higher when the machine learning model performs poorly and lower when the machine learning model performs well. In cases where the training example includes a label, the loss function is also based on the label for the training example. Some example loss functions include the mean square error function, the mean absolute error, hinge loss function, and the cross entropy loss function. The machine learning training module 230 updates the set of parameters for the machine learning model based on the score generated by the loss function. For example, the machine learning training module 230 may apply gradient descent to update the set of parameters.

The data store 240 stores data used by the online concierge system 140. For example, the data store 240 stores customer data, item data, order data, and picker data for use by the online concierge system 140. The data store 240 also stores trained machine learning models trained by the machine learning training module 230. For example, the data store 240 may store the set of parameters for a trained machine learning model on one or more non-transitory, computer-readable media. The data store 240 uses computer-readable media to store data, and may use databases to organize the stored data.

The user treatment engine 250 selects treatments to apply to users of the online concierge system 140. The user treatment engine 250 may use a guardrail setting to limit which treatments (or variations thereof) may be applied to users. The online concierge system 140 may adjust the guardrail setting for the user treatment engine 250 over time based on the conditions faced by the online concierge system 140. Additionally, the user treatment engine 250 is trained based on a set of training examples. These training examples may include real training examples based on treatments actually applied to users and simulated training examples generated based on simulated treatments applied to users. The user treatment engine 250 is described in further detail below with regards to FIG. 3-6.

Figure 3:
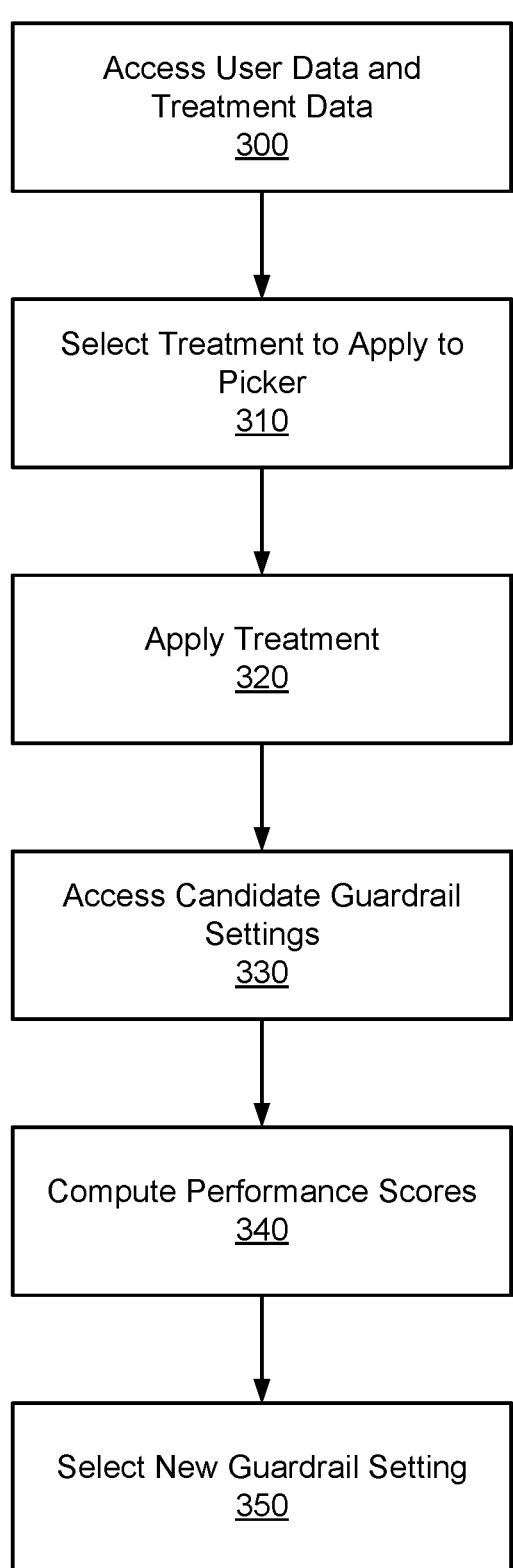
FIG. 3 is a flowchart for a method of dynamically adjusting guardrail settings for a user treatment engine, in accordance with one or more embodiments.

FIG. 3 is a flowchart for a method of dynamically adjusting guardrail settings for a user treatment engine, in accordance with some embodiments. Alternative embodiments may include more, fewer, or different steps from those illustrated in FIG. 3, and the steps may be performed in a different order from that illustrated in FIG. 3. These steps may be performed by an online concierge system (e.g., online concierge system 140). Additionally, each of these steps may be performed automatically by the online concierge system without human intervention.

The online concierge system accesses 300 user data for a set of pickers associated with the online concierge system. The user data describes characteristics of the pickers. For example, the user data may include the picker's name, the picker's location, how often the picker has serviced orders for the online concierge system, a customer rating for the picker, which retailers the picker has collected items at, or the picker's previous shopping history.

The online concierge system also accesses 300 treatment data for a set of treatments that the online concierge system may apply to the set of pickers. A treatment is an action that the online concierge system may take with regards to a user to encourage the user to interact with the online concierge system. For example, for a picker, a treatment may include notifying the picker of a possible order for servicing, offering the picker an additional service fee for servicing an order from another user, offering a temporary or permanent increase in a service fee or commission paid to the picker for servicing orders, or offering a reward to the picker for servicing a certain number of orders within a time period. A treatment may further include an encouraged interaction for the user to perform. An encouraged interaction is an interaction that is targeted by the online concierge system for the user to perform. For example, an encouraged interaction may be for a picker to service an order for the online concierge system.

Each treatment may be associated with treatment data describing the treatment. The treatment data may describe treatment parameters for the application of the treatment. For example, treatment parameters for a treatment may include timeframes when a treatment should be applied, characteristics of users to whom the treatment should be applied, a value of consideration to provide to a user or a percentage for a discount to apply to a user's order. The treatment data may also include a treatment type for each treatment. For example, the treatment type may indicate whether the treatment includes a discount, a coupon, a notification, or consideration to provide to the user. In some embodiments, the set of treatments includes multiple treatments with the same treatment type but different treatment parameters. For example, the set of treatments may include multiple discount offers, where each discount offer has a different discount percentage.

Each treatment may be associated with a cost to the online concierge system for applying the treatment to a user. For example, a treatment cost may include consideration that the online concierge system provides to a user to encourage the user to interact with the online concierge system (e.g., a discount on a product to a customer or an additional service to a picker or runner). A treatment cost also may include an opportunity cost for the online concierge system representing the lost reward to the online concierge system by applying one treatment to a user rather than a different treatment. Furthermore, a treatment cost may be based on a limited number of times the online concierge system may apply a particular treatment to any user or a limited number of times that the online concierge system may apply a treatment to a particular user. For example, the online concierge system may limit the number of notifications that it provides to a user to avoid overloading the user with too many notifications. Similarly, the online concierge system may limit the number of discounts or increased service fees that apply to users based on constraints provided by third parties to the online concierge system. Additionally, a treatment cost may be based on computer resources that are used to apply a treatment. For example, a treatment cost may be based on processing resources, networking resources, or memory resources used by the application of a treatment.

The online concierge system selects 310 a treatment to apply to the picker by executing a user treatment engine. A user treatment engine generates treatment scores for each treatment. A treatment score is a score that reflects an expected reward to the online concierge system if the associated treatment is applied to the user. To encourage the exploration of less-selected treatments, the user treatment engine may use a probability distribution (e.g., a normal distribution or a beta distribution) associated with each treatment to generate a treatment score for each treatment. The user treatment engine may adjust the treatment scores based on the user data describing the user to reflect how each treatment may be more effective for certain users over other users. Additionally, the user treatment engine may adjust the treatment scores based on treatment cost predictions associated with each treatment such that the treatment scores reflect their likely respective costs to the online concierge system for application to the user. The user treatment engine may select which treatment to apply to the user based on the treatment scores for each treatment. In some embodiments, the user treatment engine uses a multi-arm bandit algorithm to select the treatment to apply to the user. For example, the user treatment engine may use Thompson sampling to select a treatment. U.S. patent application Ser. No. 17/731,608, filed Apr. 28, 2022, describes example user treatment engines that may be used herein, and is incorporated by reference.

The online concierge system executes the user treatment engine with a guardrail setting. A guardrail setting is a setting for the user treatment engine that limits treatments or variants that the user treatment engine may select. For example, the guardrail setting may limit which types of treatments the user treatment engine may select, which variants the user treatment engine may select, or the parameters that the user treatment engine may use for a treatment. The guardrail setting may enforce a limit on a cost of an individual treatment, a total cost of a set of treatments (e.g., treatments over a time period), or a frequency of how often a particular treatment is selected.

The online concierge system applies 320 the selected treatment to the picker. The online concierge system may apply the selected treatment to the picker by transmitting instructions to a picker device associated with the picker to display a message associated with the treatment. For example, the online concierge system may transmit instructions to a picker device associated with a picker instructing the picker device to display and offer an increased service fee to the picker user if the picker user services at least a threshold number of orders within a certain time period.

The online concierge system selects a new guardrail setting for the user treatment engine by simulating the performance of a set of candidate guardrail settings. The online concierge system accesses 330 a set of candidate guardrail settings for the user treatment engine and computes 340 a performance score for each of the candidate guardrail settings. A performance score represents a predicted performance of the user treatment engine when using the candidate guardrail setting. The user treatment engine's performance is scored based on how well its selection of treatments to apply to pickers ensures that a sufficient number of pickers are available to service a predicted number of orders to be received by the online concierge system within some upcoming time period. In other words, the performance score represents how well the candidate guardrail setting allows the user treatment engine to select treatments that ensure a sufficient supply of pickers are active to service the predicted demand from customers.

The online concierge system simulates the performance of the user treatment engine with a candidate guardrail setting by simulating the execution of the user treatment engine with the candidate guardrail setting. For example, the user treatment engine may iteratively select a set of treatments using the candidate guardrail setting for a certain number of iterations and evaluate the performance of the user treatment engine based on the selected set of treatments. The online concierge system may perform multiple simulations for each candidate guardrail setting, where each simulation includes iterations where the user treatment engine iteratively selects treatments to apply to pickers. The online concierge system may aggregate the results of the user treatment engine to determine its overall performance with a candidate guardrail setting. In some embodiments, the online concierge system uses a Monte Carlo simulation to simulate the performance of the user treatment engine.

The online concierge system may use parameters stored by the user treatment engine representing a predicted outcome for a treatment to predict the outcome of each treatment in the selected set of treatments. For example, if the user treatment engine has a probability distribution for each treatment type that represents the likelihood that each treatment will be successful, the online concierge system may sample from a selected treatment's probability distribution when determining the outcome of the selected treatment within the simulation for a guardrail setting.

The online concierge system compares the simulated performances of the user treatment engine to a predicted number of future orders. The predicted number of future orders is a predicted number of orders that the online concierge system expects to receive within some time period in the future. For example, the online concierge system may predict the number of orders that the online concierge system expects to receive within the next 24 hours. The online concierge system may predict an expected number of received orders by using an order prediction model. An order prediction model is a machine-learning model that is trained to predict a number of orders that the online concierge system will receive within some time period. The order prediction model may predict the number of future orders based on order data for previous orders (e.g., orders within some previous time period), user data, retailer data, or weather data.

The online concierge system computes the performance score for a candidate guardrail setting based on the comparison of predicted number of future orders to the simulated performance of the user treatment engine corresponding to the guardrail setting. For example, the online concierge system may estimate the number of orders that pickers would service based on the set of treatments selected by the user treatment engine as part of the performance simulations. The online concierge system computes the performance score based on the difference between that estimated number of orders that pickers would service and the predicted number of future orders. In other words, the online concierge system may compute the performance score based on a difference in a predicted demand for orders from customers and a simulated supply of order servicing by pickers.

FIG. 5 illustrates example performance scores 500 for a set of candidate guardrail settings 510, in accordance with some embodiments. The illustrated guardrail settings 510 represent a maximum for bonus consideration that the online concierge system may provide to a picker if the picker services a certain number of orders within a time period. The online concierge system predicts 520 a number of orders that users will service if the user treatment engine is executed with a corresponding guardrail setting 510. The online concierge system computes the performance score 500 for each guardrail setting 510 based on a comparison of the guardrail setting's corresponding prediction 520 and a predicted number 530 of orders that the online concierge system expects to receive over the same corresponding time period (e.g., in the next hour).

The online concierge system selects 350 a new guardrail setting for the user treatment engine based on the computed performance scores for the candidate guardrail settings. The online concierge system may rank the candidate guardrail settings based on their performance scores and select, as the new guardrail setting, the candidate guardrail setting with the best performance score. The online concierge system uses the new guardrail setting for the user treatment model for selecting treatments for future users.

In some embodiments, the online concierge system regularly selects a new guardrail setting using the method described above. For example, the online concierge system may select a new guardrail setting periodically (i.e., after an interval of time) or in response to the predicted number of future orders changing significantly within some period of time.

Figure 4:
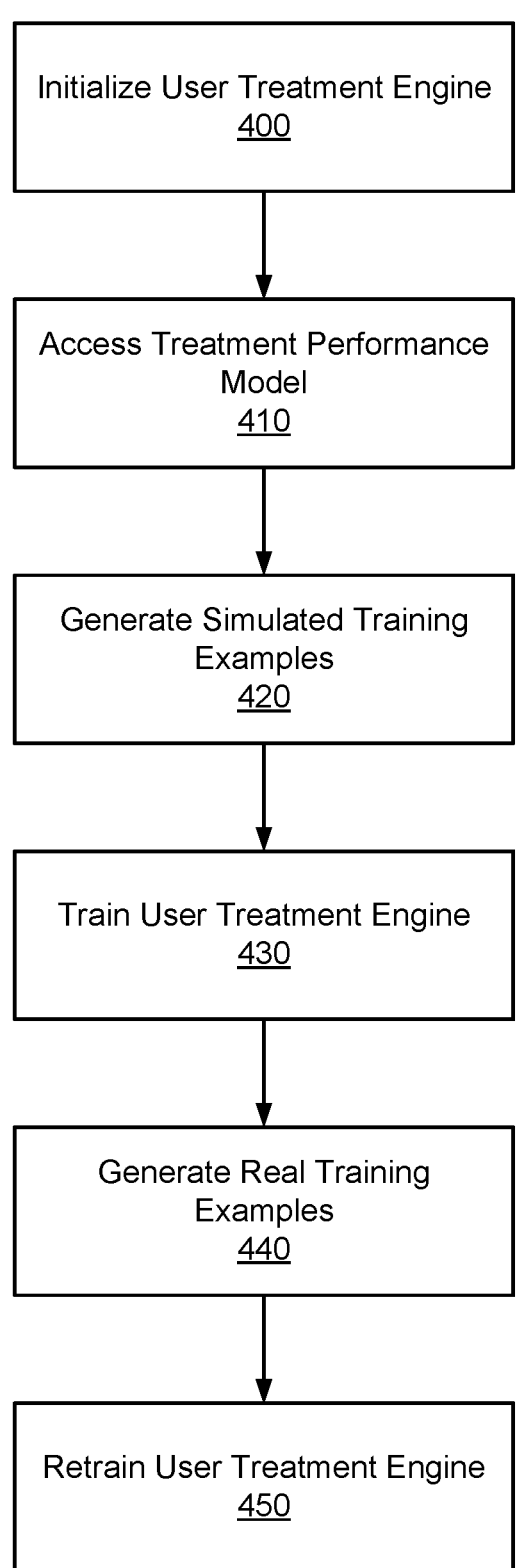
FIG. 4 is a flowchart for a method of generating simulated training data for a user treatment engine using a treatment performance model, in accordance with one or more embodiments.

FIG. 4 is a flowchart for a method of generating simulated training data for a user treatment engine using a treatment performance model, in accordance with some embodiments. Alternative embodiments may include more, fewer, or different steps from those illustrated in FIG. 4, and the steps may be performed in a different order from that illustrated in FIG. 4. These steps may be performed by an online concierge system (e.g., online concierge system 140). Additionally, each of these steps may be performed automatically by the online concierge system without human intervention.

The online concierge system initializes 400 a user treatment engine to select treatments and treatment variants to apply to users. The user treatment engine includes a multi-armed bandit model to be used to select which treatments or variants to apply. The online concierge system may initialize the user treatment engine by creating the user treatment engine with a set of default parameters. For example, the online concierge system may generate a multi-armed bandit model for the user treatment engine that has a set of default reward probability distributions for each treatment type or variant.

The online concierge system accesses 410 a treatment performance model. A treatment performance model is a machine-learning model (e.g., a neural network) that is trained to predict a number of orders that a user will service within a time period after that user has been applied with a treatment. For example, the treatment performance model may predict a number of orders a user will service within twenty-four hours after the online concierge system applied a treatment to the user. The treatment performance model is trained to make predictions based on user data describing a user to whom a treatment has been applied and treatment data describing the applied treatment.

The online concierge system may train the treatment performance model based on a set of training examples. Each training example includes user data for a user to whom the online concierge system applied a treatment and treatment data describing the treatment applied to the user. Each training example also includes a label indicating a number of orders serviced by the user within some time period after the treatment was applied to the users.

The online concierge system generates 420 a set of simulated training examples using the treatment performance model. To generate a simulated training example, the online concierge system may simulate the application of a treatment to a user using the treatment performance model. For example, the online concierge system may apply the treatment performance model to user data for a user and treatment data for a treatment to simulate applying to the user. The treatment performance model outputs a predicted number of orders that the user would service if the online concierge system had applied the treatment to the user. The online concierge system generates a simulated training example based on the user data for the user and treatment data for the treatment. The online concierge system also assigns the simulated training example a label that indicates the predicted number of orders that the treatment performance model output based on the corresponding user data and treatment data.

The online concierge system trains 430 the user treatment engine based on the generated set of simulated training examples. The online concierge system may generate sufficient simulated training examples such that the user treatment engine, once trained, can select treatments to apply to users with some threshold level of efficacy. For example, the online concierge system may generate a minimum number of simulated training examples. The online concierge system also may generate a number of simulated training examples that corresponds to a number of typical training examples that would be generated during a period of time. For example, the online concierge system may generate one or two weeks' worth of simulated training examples.

The online concierge system applies the user treatment engine to select treatments to apply to users of the online concierge system, and generates 440 a set of real training examples based on the applied treatments. A real training example is similar to a simulated training example, except a real training example reflects the effects on a user that has actually been applied with a treatment, whereas a simulated training example represents a simulated treatment applied to a user. The online concierge system generates the real training examples based on how many orders a user services after being applied with a treatment selected by the user treatment engine. For example, the online concierge system may generate a real training example based on user data for a user to whom a treatment was applied and treatment data for the treatment that the user treatment engine selected to be applied to the user. The online concierge system labels the real training example based on the number of orders the user services after being applied with the treatment. In some embodiments, the online concierge system labels the real training example based on the number of serviced orders within some time period after the user was treated (e.g., within 24 hours).

The online concierge system retrains 450 the user treatment engine based on the generated real training examples. The online concierge system may continually retrain the user treatment engine as the online concierge system generates the real training examples. For example, the online concierge system may retrain the user treatment engine based on a combined set of training examples that includes a subset of the simulated training examples and real training examples generated by the online concierge system. As the online concierge system uses the user treatment engine to select treatments to apply to users, the online concierge system generates more real training examples and adds these training examples to the set of training examples used to train the user treatment engine. Similarly, as the online concierge system adds real training examples to the combined set, the online concierge system may remove simulated training examples. Thus, the combined set may eventually only contain real training examples and the user treatment engine is retrained based only on real training examples, and on none of the simulated training examples.

FIG. 6 illustrates example sets of training examples that may be used to train or retrain a user treatment engine, in accordance with some embodiments. FIG. 6 illustrates training examples that may be generated by the online concierge system over time. The online concierge system may generate the simulated training examples using a treatment performance model, as described above. The online concierge system may use this set of simulated training examples as a set of training examples 600 for training an initialized user treatment engine. As the online concierge system generates real training examples based on treatments selected by the user treatment engine, the online concierge system may use another set of training examples 610 that includes a subset of the simulated training examples and a set of real training examples that had been generated up to that point. Eventually, the online concierge system may use a set of training examples 620 that exclusively contains real training examples.

Figure 7A:
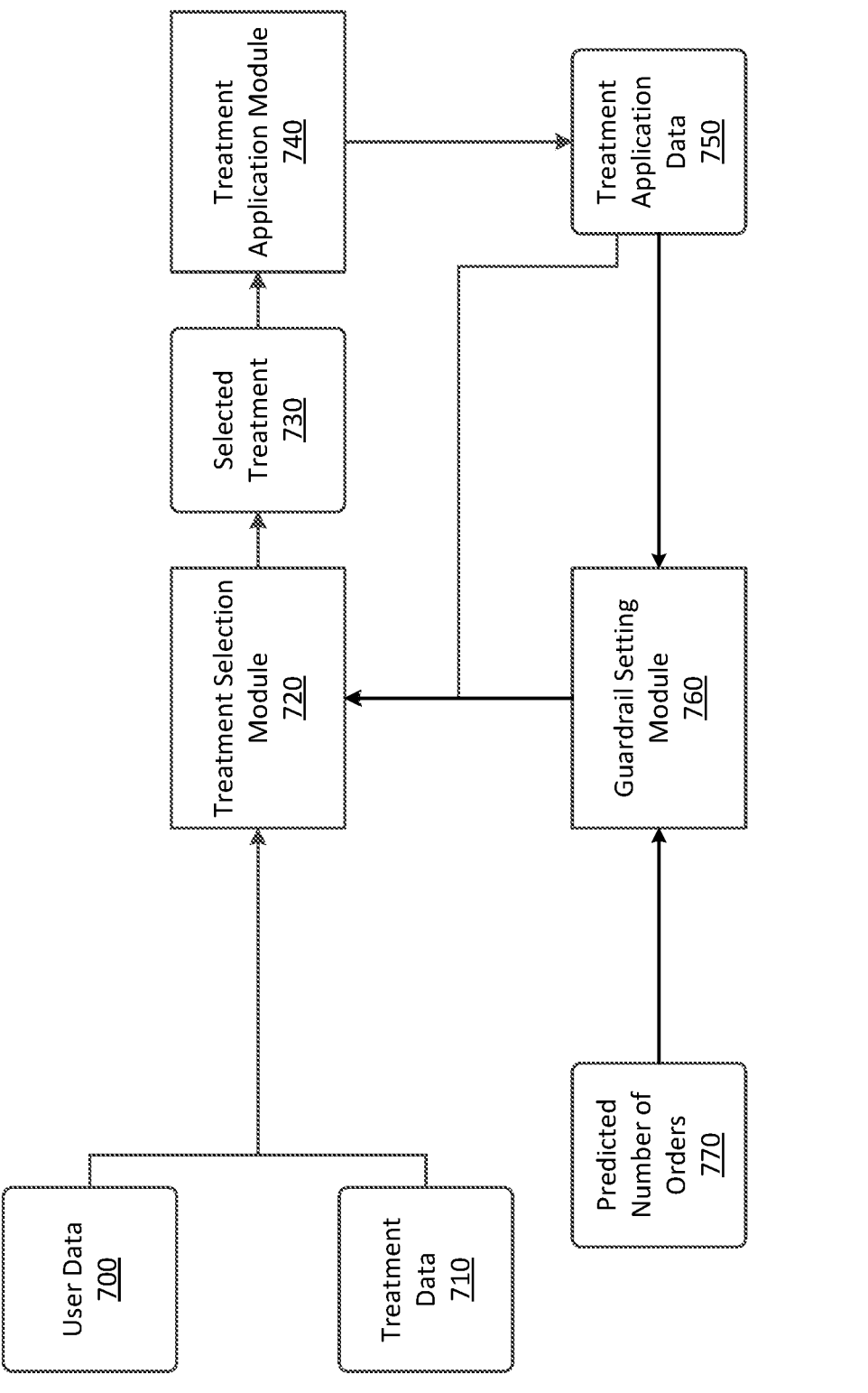
FIG. 7A illustrates an example system architecture and data flow for a user treatment engine that dynamically adjusts guardrail settings used to select treatments for application to users, in accordance with one or more embodiments.

FIG. 7A illustrates an example system architecture and data flow for a user treatment engine that dynamically adjusts guardrail settings used to select treatments for application to users, in accordance with some embodiments. Alternative embodiment may include more, fewer, or different components from those illustrated in FIG. 7A and the functionality of each component may differ from the description below.

The user treatment engine receives user data 700 describing characteristics of a user and treatment data 710 describing characteristics of a set of candidate treatments. A treatment selection module 720 uses the user data 700 and the treatment data 710 to select a treatment 730 to apply to the user corresponding to the user data 700. The treatment selection module may use a machine-learned treatment selection model, such as a multi-armed bandit model, to select which treatment to apply to the user. The treatment application module 740 applies the selected treatment 730 to the user and collects treatment application data 750 which describes characteristics of the application of the treatment to the user (e.g., whether and to what extent the treatment was successful). The treatment application module 740 provides the treatment application data 750 to the treatment selection module 720 to further train the treatment selection model used by the treatment selection module 720.

The treatment selection module 720 uses a guardrail setting to select the treatment 730 to apply to the user. The guardrail setting module 760 dynamically adjusts the guardrail setting used by the treatment selection module 720 based on the conditions faced by the online concierge system. The guardrail setting module 760 receives a predicted number of orders 770 that the online concierge system expects to receive from users within a period of time and simulates the performance of the treatment selection module 720 based on how well the treatment selection module 720 selects treatments such that a sufficient number of pickers are available to service the predicted number of orders 770. As described above, the guardrail setting module 760 simulates the performance of each of a set of candidate guardrail settings and scores each of the candidate guardrail settings based on their performance during the simulations. The guardrail setting module 760 selects a new guardrail setting for the treatment selection module 720 based on the scores for each of the candidate guardrail settings.

Figure 7B:
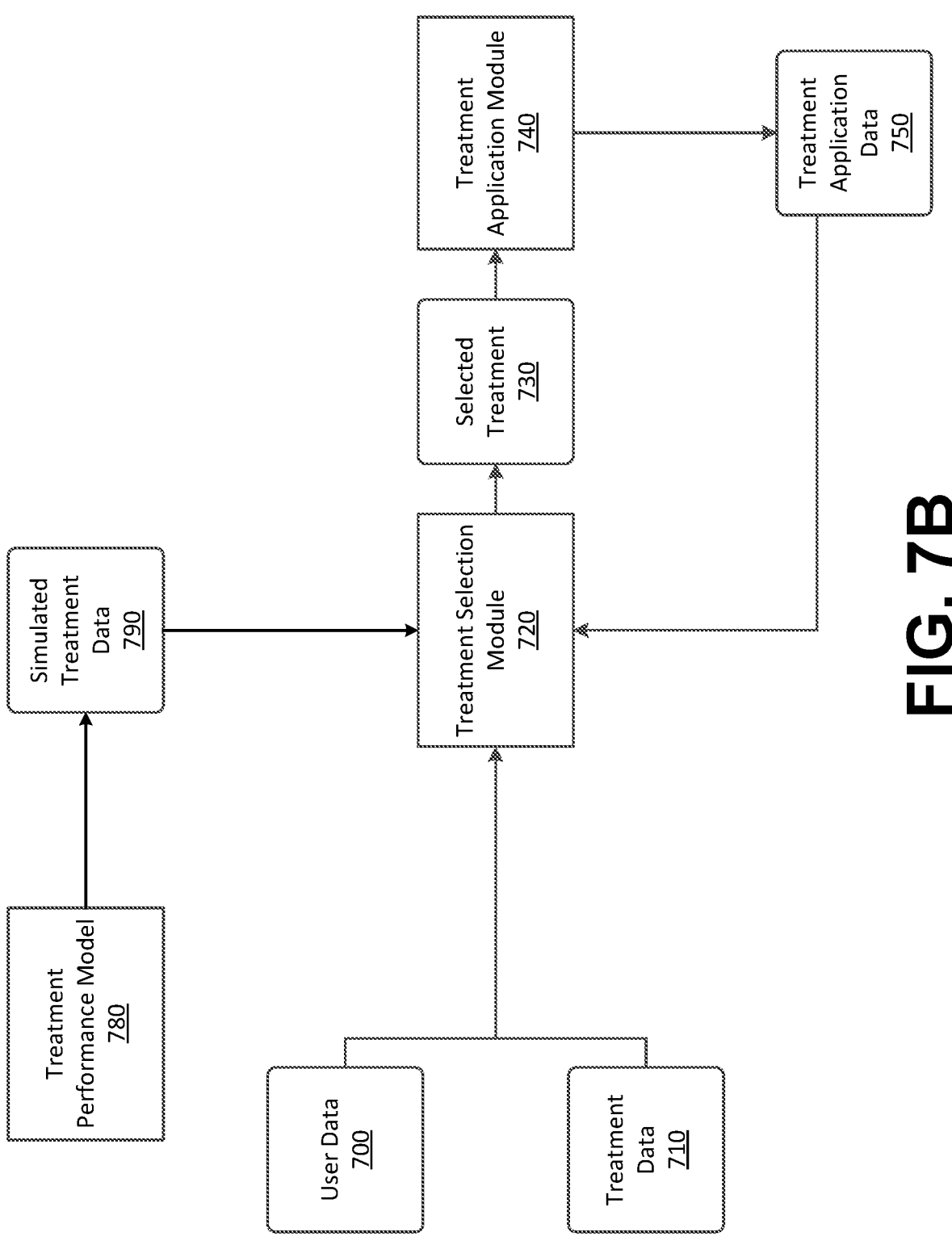
FIG. 7B illustrates an example system architecture and data flow for a user treatment engine that uses simulated training data from a treatment performance model, in accordance with one or more embodiments.

FIG. 7B illustrates an example system architecture and data flow for a user treatment engine that uses simulated training data from a treatment performance model, in accordance with some embodiments. Alternative embodiment may include more, fewer, or different components from those illustrated in FIG. 7B and the functionality of each component may differ from the description below.

The online concierge system may initialize the user treatment engine such that a multi-armed bandit model used by the treatment selection module 720 has a set of default parameters for selecting treatments. To train the multi-armed bandit model, a treatment performance model 780 generates simulated treatment data 790 that describes simulated applications of treatments to users. The simulated treatment data 790 includes simulated training examples that the treatment selection module 720 uses to train the multi-armed bandit model. The treatment selection module 720 uses the trained multi-armed bandit model to select treatments 730 to apply to users.

As the treatment application module 740 applies treatments that have been selected by the treatment selection module 720, the treatment application module 740 collects treatment application data 750 that describes the application of the treatments to the users. The treatment application data 750 includes real training examples, which the treatment application module 740 may provide back to the treatment selection module 720 to train the multi-armed bandit model. As described above, the treatment selection module 720 may adjust how many simulated training examples the multi-armed bandit model uses to select treatments as the treatment selection module 720 receives real training examples in treatment application data from the treatment application module 740. Eventually, the treatment selection module 720 may solely use real training examples to train the multi-armed bandit model.

Figure 7C:
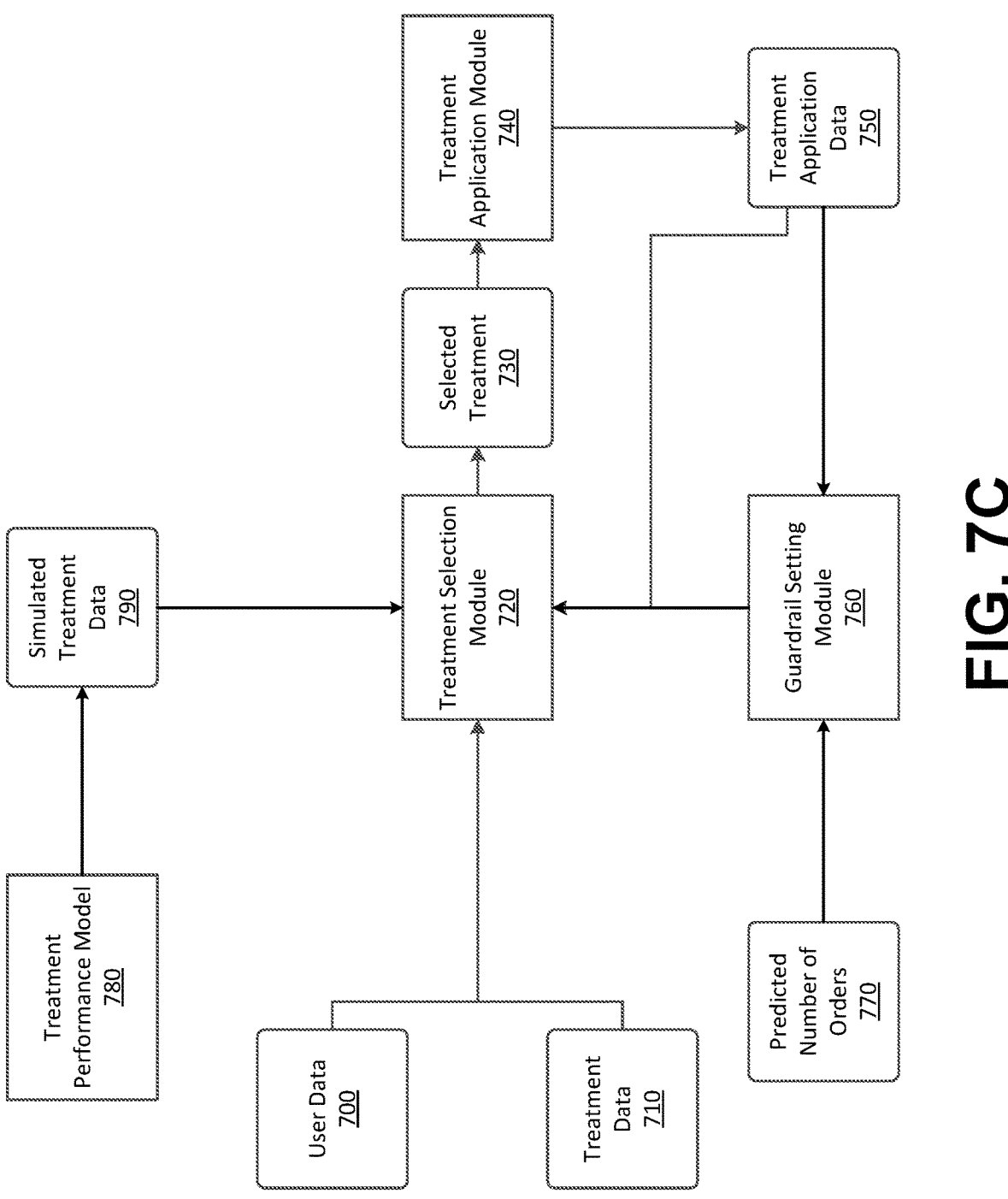
FIG. 7C illustrates an example system architecture and data flow for a user treatment engine that dynamically adjusts guardrail settings and uses simulated training data from a treatment performance model, in accordance with one or more embodiments.

FIG. 7C illustrates an example system architecture and data flow for a user treatment engine that dynamically adjusts guardrail settings and uses simulated training data from a treatment performance model, in accordance with some embodiments. Alternative embodiment may include more, fewer, or different components from those illustrated in FIG. 7C and the functionality of each component may differ from the description below.

As demonstrated with FIG. 7C, an online concierge system may include a user treatment engine with the combined functionality of user treatment engines described FIGS. 7A and 7B. For example, the user treatment engine may include a guardrail setting module 760 that dynamically adjusts guardrail settings for the treatment selection module 720, and may use simulated treatment data 790 from a treatment performance model 780 to train a newly initialized user treatment engine.

Additional Considerations

The foregoing description of the embodiments has been presented for the purpose of illustration; many modifications and variations are possible while remaining within the principles and teachings of the above description.

Any of the steps, operations, or processes described herein may be performed or implemented with one or more hardware or software modules, alone or in combination with other devices. In some embodiments, a software module is implemented with a computer program product comprising one or more computer-readable media storing computer program code or instructions, which can be executed by a computer processor for performing any or all of the steps, operations, or processes described. In some embodiments, a computer-readable medium comprises one or more computer-readable media that, individually or together, comprise instructions that, when executed by one or more processors, cause the one or more processors to perform, individually or together, the steps of the instructions stored on the one or more computer-readable media. Similarly, a processor comprises one or more processors or processing units that, individually or together, perform the steps of instructions stored on a computer-readable medium.

Embodiments may also relate to a product that is produced by a computing process described herein. Such a product may store information resulting from a computing process, where the information is stored on a non-transitory, tangible computer-readable medium and may include any embodiment of a computer program product or other data combination described herein.

The description herein may describe processes and systems that use machine learning models in the performance of their described functionalities. A "machine learning model," as used herein, comprises one or more machine learning models that perform the described functionality. Machine learning models may be stored on one or more computer-readable media with a set of weights. These weights are parameters used by the machine learning model to transform input data received by the model into output data. The weights may be generated through a training process, whereby the machine learning model is trained based on a set of training examples and labels associated with the training examples. The training process may include: applying the machine learning model to a training example, comparing an output of the machine learning model to the label associated with the training example, and updating weights associated for the machine learning model through a back-propagation process. The weights may be stored on one or more computer-readable media, and are used by a system when applying the machine learning model to new data.

The language used in the specification has been principally selected for readability and instructional purposes, and it may not have been selected to narrow the inventive subject matter. It is therefore intended that the scope of the patent rights be limited not by this detailed description, but rather by any claims that issue on an application based hereon.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive "or" and not to an exclusive "or". For example, a condition "A or B" is satisfied by any one of the following: A is true (or present) and B is false (or not present), A is false (or not present) and B is true (or present), and both A and B are true (or present). Similarly, a condition "A, B, or C" is satisfied by any combination of A, B, and C being true (or present). As a not-limiting example, the condition "A, B, or C" is satisfied when A and B are true (or present) and C is false (or not present). Similarly, as another not-limiting example, the condition "A, B, or C" is satisfied when A is true (or present) and B and C are false (or not present).

What is claimed is:

1. A method comprising, at a computer system comprising a processor and a computer-readable medium:

initializing a user treatment engine comprising a multi-armed bandit model for selecting treatments to apply to users;

accessing a treatment performance model, wherein the treatment performance model is a machine-learning model that is trained to predict a number of orders that will be serviced by a user within a time period after a treatment is applied to the user by an online concierge system, wherein the treatment performance model is trained to make predictions based on treatment data describing the treatment applied to the user and user data describing the user;

generating a set of simulated training examples for the user treatment engine by applying the treatment performance model to user data for a first plurality of users and treatment data for a set of treatments, wherein each simulated training example of the set of simulated training examples indicates a predicted number of orders to be serviced by a user of the first plurality of users after a treatment of the set of treatments is applied to the user;

training the user treatment engine based on the set of simulated training examples;

generating a set of real training examples by applying treatments to a second plurality of users of the online concierge system, wherein the applied treatments are selected by the user treatment engine based on user data associated with the second plurality of users, wherein applying a treatment to a user of the second plurality of users comprises:

transmitting instructions to a client device associated with the user of the second plurality of users, wherein the instructions cause the client device to present content to the user based on a treatment of the applied treatments;

receiving data from the client device describing user interactions by the user with the presented content through the client device; and generating a real training example comprising user data associated with the user of the second plurality of users, treatment data for the treatment of the applied treatments, and a label describing the data describing the user interactions by the user;

retraining the user treatment engine based on the set of real training examples and a subset of the simulated training examples;

accessing user data associated with a target user of the online concierge system;

generating a score for a candidate treatment by applying the user treatment engine to the accessed user data and treatment data for the candidate treatment; and applying the candidate treatment to the user based on the generated score, wherein applying the candidate treatment comprises transmitting content relating to the treatment to a client device associated with the target user for display to the target user.

2. The method of claim 1, wherein initializing the user treatment engine comprises:

storing the multi-armed bandit model with a set of default parameters.

3. The method of claim 1, wherein the treatment performance model is a neural network.

4. The method of claim 1, further comprising:

training the treatment performance model based on a set of training examples, wherein each training example indicates a number of orders serviced by a user within the time period after a treatment is applied to the user.

5. The method of claim 1, wherein the time period is at least one of: 24 hours after a treatment is applied to a user, 48 hours after a treatment is applied to a user, or a week after a treatment is applied to a user.

6. The method of claim 1, wherein generating the set of simulated training examples comprises:

generating a minimum number of simulated training examples.

7. The method of claim 1, further comprising:

continually retraining the user treatment engine based on an increasing number of generated real training examples and a decreasing number of simulated training examples.

8. The method of claim 7, wherein continually retraining the user treatment engine comprises:

training the user treatment engine based on real training examples and based on none of the generated set of simulated training examples.

9. The method of claim 1, wherein generating the set of real training examples comprises:

selecting treatments to apply to the second plurality of users based on the user treatment engine, wherein the user treatment engine uses a guardrail setting to limit which treatments of a set of candidate treatments may be selected.

10. The method of claim 9, further comprising:

selecting a new guardrail setting for the user treatment engine.

11. A non-transitory computer-readable medium storing instructions that, when executed by a processor, cause the processor to:

initialize a user treatment engine comprising a multi-armed bandit model for selecting treatments to apply to users;

access a treatment performance model, wherein the treatment performance model is a machine-learning model that is trained to predict a number of orders that will be serviced by a user within a time period after a treatment is applied to the user by an online concierge system, wherein the treatment performance model is trained to make predictions based on treatment data describing the treatment applied to the user and user data describing the user;

generate a set of simulated training examples for the user treatment engine by applying the treatment performance model to user data for a first plurality of users and treatment data for a set of treatments, wherein each simulated training example of the set of simulated training examples indicates a predicted number of orders to be serviced by a user of the first plurality of users after a treatment of the set of treatments is applied to the user;

train the user treatment engine based on the set of simulated training examples;

generate a set of real training examples by applying treatments to a second plurality of users of the online concierge system, wherein the applied treatments are selected by the user treatment engine based on user data associated with the second plurality of users, wherein applying a treatment to a user of the second plurality of users comprises:

transmitting instructions to a client device associated with the user of the second plurality of users, wherein the instructions cause the client device to present content to the user based on a treatment of the applied treatments;

receiving data from the client device describing user interactions by the user with the presented content through the client device; and generating a real training example comprising user data associated with the user of the second plurality of users, treatment data for the treatment of the applied treatments, and a label describing the data describing the user interactions by the user;

retrain the user treatment engine based on the set of real training examples and a subset of the simulated training examples;

access user data associated with a target user of the online concierge system;

generate a score for a candidate treatment by applying the user treatment engine to the accessed user data and treatment data for the candidate treatment; and apply the candidate treatment to the user based on the generated score, wherein applying the candidate treatment comprises transmitting content relating to the treatment to a client device associated with the target user for display to the target user.

12. The computer-readable medium of claim 11, wherein the instructions for initializing the user treatment engine comprise instructions that cause the processor to:

store the multi-armed bandit model with a set of default parameters.

13. The computer-readable medium of claim 11, wherein the treatment performance model is a neural network.

14. The computer-readable medium of claim 11, further storing instructions that cause the processor to:

train the treatment performance model based on a set of training examples, wherein each training example indicates a number of orders serviced by a user within the time period after a treatment is applied to the user.

15. The computer-readable medium of claim 11, wherein the time period is at least one of: 24 hours after a treatment is applied to a user, 48 hours after a treatment is applied to a user, or a week after a treatment is applied to a user.

16. The computer-readable medium of claim 11, wherein the instructions for generating the set of simulated training examples comprise instructions that cause the processor to:

generate a minimum number of simulated training examples.

17. The computer-readable medium of claim 11, further storing instructions that cause the processor to:

continually retrain the user treatment engine based on an increasing number of generated real training examples and a decreasing number of simulated training examples.

18. The computer-readable medium of claim 17, wherein the instructions for continually retraining the user treatment engine comprise instructions that cause the processor to:

train the user treatment engine based on real training examples and based on none of the generated set of simulated training examples.

19. The computer-readable medium of claim 11, wherein the instructions for generating the set of real training examples comprise instructions that cause the processor to:

select treatments to apply to the second plurality of users based on the user treatment engine, wherein the user treatment engine uses a guardrail setting to limit which treatments of a set of candidate treatments may be selected.

20. A system comprising:

a processor; and a non-transitory computer-readable medium storing instructions that, when executed by the processor, cause the system to:

initialize a user treatment engine comprising a multi-armed bandit model for selecting treatments to apply to users;

access a treatment performance model, wherein the treatment performance model is a machine-learning model that is trained to predict a number of orders that will be serviced by a user within a time period after a treatment is applied to the user by an online concierge system, wherein the treatment performance model is trained to make predictions based on treatment data describing the treatment applied to the user and user data describing the user;

generate a set of simulated training examples for the user treatment engine by applying the treatment performance model to user data for a first plurality of users and treatment data for a set of treatments, wherein each simulated training example of the set of simulated training examples indicates a predicted number of orders to be serviced by a user of the first plurality of users after a treatment of the set of treatments is applied to the user;

train the user treatment engine based on the set of simulated training examples;

generate a set of real training examples by applying treatments to a second plurality of users of the online concierge system, wherein the applied treatments are selected by the user treatment engine based on user data associated with the second plurality of users, wherein applying a treatment to a user of the second plurality of users comprises:

transmitting instructions to a client device associated with the user of the second plurality of users, wherein the instructions cause the client device to present content to the user based on a treatment of the applied treatments;

receiving data from the client device describing user interactions by the user with the presented content through the client device; and generating a real training example comprising user data associated with the user of the second plurality of users, treatment data for the treatment of the applied treatments, and a label describing the data describing the user interactions by the user;

retrain the user treatment engine based on the set of real training examples and a subset of the simulated training examples;

access user data associated with a target user of the online concierge system;

generate a score for a candidate treatment by applying the user treatment engine to the accessed user data and treatment data for the candidate treatment; and apply the candidate treatment to the user based on the generated score, wherein applying the candidate treatment comprises transmitting content relating to the treatment to a client device associated with the target user for display to the target user.

\* \* \* \* \*